US010271981B2

(12) United States Patent
Raniere (10) Patent No.: US 10,271,981 B2
(45) Date of Patent: Apr. 30, 2019

(54) COMBINATION WOUND AND INJURY TREATMENT APPARATUS

(71) Applicant: FIRST PRINCIPLES, INC., Albany, NY (US)

(72) Inventor: Keith A. Raniere, Clifton Park, NY (US)

(73) Assignee: FIRST PRINCIPLES, INC., Albany, NY (US)

(*) Notice: Subject to any disclaimer, the term of this patent is extended or adjusted under 35 U.S.C. 154(b) by 800 days.

(21) Appl. No.: 13/841,450

(22) Filed: Mar. 15, 2013

(65) Prior Publication Data

US 2014/0276256 A1    Sep. 18, 2014

(51) Int. Cl.
*A61F 5/01* (2006.01)
*A61F 7/02* (2006.01)
*A61F 13/00* (2006.01)
*A61F 13/06* (2006.01)
(Continued)

(52) U.S. Cl.
CPC .............. *A61F 5/012* (2013.01); *A61F 7/02* (2013.01); *A61F 13/00029* (2013.01); *A61F 13/06* (2013.01); *A61F 13/085* (2013.01); *A61F 2007/0043* (2013.01); *A61F 2007/0091* (2013.01); *A61F 2007/023* (2013.01); *A61F 2007/0219* (2013.01); *A61F 2013/0028* (2013.01); *A61F 2013/00093* (2013.01); *A61F 2013/00174* (2013.01); *A61F 2013/00187* (2013.01); *A61F 2013/00272* (2013.01); *A61F 2013/00468* (2013.01);
(Continued)

(58) Field of Classification Search
CPC .......... A61H 7/001; A61H 9/00; A61H 9/005; A61H 9/0078; A61H 9/0085; A61H 9/0092; A61H 2201/0107; A61H 2201/0103; A61F 5/012; A61F 5/05816; A61F 5/30; A61F 5/32; A61F 5/34
See application file for complete search history.

(56) References Cited

U.S. PATENT DOCUMENTS 2,245,909 A    6/1941  Enfiajian
2,832,336 A    4/1958  Davis et al.
(Continued)

FOREIGN PATENT DOCUMENTS

WO    2006/110028 A1    10/2006

*Primary Examiner* — Michael J Tsai
(74) *Attorney, Agent, or Firm* — Schmeiser, Olsen & Watts, LLP (57) ABSTRACT

Disclosed herein is a combination wound and injury treatment apparatus including a tubular body having a first opening, a second opening, a relatively inflexible outer wall having an outer surface and an inner surface, a relatively flexible inner wall having an inner surface and an outer surface, an upper end member having an inner surface and an outer surface, and a lower end member having an inner surface and an outer surface, the first opening, the inner surface of the relatively flexible inner wall and the second opening define a passage through the tubular body for receiving a body part. Structure is formed between the inner surface and the outer surface of the inner wall, the structure being capable of receiving a temperature retaining fluid, and a pressurized chamber, operatively formed between the inner surface of the outer wall and the outer surface of the inner wall.

13 Claims, 3 Drawing Sheets

(51) Int. Cl.
*A61F 13/08* (2006.01)
*A61F 7/00* (2006.01)

(52) U.S. Cl.
CPC ............... *A61F 2013/00553* (2013.01); *A61F 2013/00574* (2013.01); *A61F 2013/00578* (2013.01)

(56) References Cited

U.S. PATENT DOCUMENTS

| | | | |
|---|---|---|---|
| 3,561,435 A * | 2/1971 | Nicholson | A61F 5/05816 128/DIG. 20 |
| 3,826,249 A * | 7/1974 | Lee | A61B 17/135 128/DIG. 20 |
| 3,862,629 A * | 1/1975 | Rotta | A61H 9/0078 128/DIG. 10 |
| 4,029,087 A * | 6/1977 | Dye | A61B 17/135 601/152 |
| 4,146,021 A | 3/1979 | Brousseau et al. | |
| 4,372,297 A | 2/1983 | Perlin | |
| 4,531,516 A * | 7/1985 | Poole | A61F 5/05816 128/DIG. 20 |
| 4,624,248 A * | 11/1986 | Poole | A61F 5/05816 128/DIG. 20 |
| 4,805,601 A | 2/1989 | Eischen, Sr. | |
| 4,964,402 A * | 10/1990 | Grim | A61F 5/0111 602/2 |
| 5,074,285 A | 12/1991 | Wright | |
| 5,088,478 A | 2/1992 | Grim | |
| 5,288,286 A | 2/1994 | Davis | |
| 5,407,421 A * | 4/1995 | Goldsmith | A61F 5/012 128/882 |
| 5,466,250 A | 11/1995 | Johnson, Jr. et al. | |
| 5,486,206 A * | 1/1996 | Avery | A61F 7/02 607/104 |
| 5,695,452 A | 12/1997 | Grim et al. | |
| 5,711,760 A | 1/1998 | Ibrahim et al. | |
| 5,868,690 A * | 2/1999 | Eischen, Sr. | A61H 9/0078 128/DIG. 20 |
| 5,980,435 A | 11/1999 | Joutras et al. | |
| 6,010,471 A * | 1/2000 | Ben-Noon | A61F 5/05816 601/149 |
| 6,083,254 A * | 7/2000 | Evans | A61F 7/02 607/108 |
| 6,416,534 B1 | 7/2002 | Montagnino et al. | |
| 6,554,787 B1 | 4/2003 | Griffin et al. | |
| 6,585,673 B1 | 7/2003 | Bass | |
| 6,656,141 B1 | 12/2003 | Reid | |
| 6,757,916 B2 | 7/2004 | Mah et al. | |
| 2001/0027282 A1 | 10/2001 | Baugh | |
| 2003/0125650 A1 | 7/2003 | Grosso | |
| 2005/0043660 A1 | 2/2005 | Stark et al. | |
| 2005/0070828 A1 | 3/2005 | Hampson et al. | |
| 2005/0154336 A1 | 7/2005 | Bloecker et al. | |
| 2005/0159690 A1 | 7/2005 | Barak et al. | |
| 2010/0137764 A1* | 6/2010 | Eddy | A61H 9/0078 601/152 |
| 2011/0034840 A1* | 2/2011 | Broun | A61H 9/0071 601/152 |
| 2011/0087143 A1* | 4/2011 | Bobey | A61H 9/0078 601/152 |
| 2014/0276258 A1* | 9/2014 | Hall | A61H 1/008 601/18 |

\* cited by examiner

COMBINATION WOUND AND INJURY TREATMENT APPARATUS

BACKGROUND OF THE DISCLOSURE

The present disclosure is directed to a combination wound and injury treatment apparatus, and more particularly, to a pressurized wound and injury treatment apparatus that may include thermal packs that may be positioned on a patient's body part to provide circumferential thermal treatment at a desired location on the body part and/or pressurized sterile material for the treatment of wounds and/or injuries.

The generally accepted first aid treatment for injuries such as, for example, strains, sprains, contusions, dislocations, uncomplicated fractures and other non-acute injuries to human body parts may be often referred to by the acronym RICE, which stands for rest, ice, compression and elevation. Rest may be prescribed because continued activity may cause further injury to the body part thereby delaying the healing process, increasing pain, and stimulating internal bleeding. Ice may be prescribed because blood vessels contract when exposed to cold temperatures, which helps reduce swelling in the injured body part and also helps to reduce the extent of internal bleeding from injured capillaries and blood vessels. Compression may be prescribed because it tends to hasten healing time by reducing swelling around the injury. And, elevation of the body part above the heart may be prescribed because it tends to reduce swelling in the body part and also tends to reduce pain.

Although ice may be prescribed to treat injured body parts, ice may cause discomfort when placed between a compressive wrap and an injured body part because it may be a rigid non-conforming solid. Ice may be also difficult to position on an injured body part, and it tends to melt quickly, which results in a loss of the desired cold treatment and/or frequent disturbance of the injured body part to apply more ice. In view of these and other disadvantages, temperature-retaining gel-filled thermal packs may be frequently used instead of ice in the first aid treatment of injured body parts. The gels used in such packs tend to remain cold for a longer period of time than ice, and such gels also preferably remain viscous at low temperatures, which allow them to more comfortably conform to the contours of the injured body part when placed between a compressive wrap and the injured body part.

Flat packs, while widely used to provide first aid treatment to injured body parts, present certain problems and disadvantages. One problem with flat packs may be that they do not provide circumferential thermal treatment to injured body parts (i.e., thermal treatment completely surrounding the injured body part at the location of the injury). Flat packs may be effective in applying cold treatment to injured body parts only insofar as they may be placed into contact with the injured body part. Thus, in order to provide circumferential or radial thermal treatment to an injured body part, it may be typically necessary to apply more than one flat pack to the injured body part, which may present placement and retention problems. In addition, it may be sometimes very difficult and time consuming to secure flat packs to an injured body part, even when the flat pack may be provided with straps or other securing means Concerning wounds, one of the leading causes of death on military battlegrounds and in hospital trauma units may be severe blood loss and the associated shock that it produces. Therefore, one of the most vital priorities of caregivers (medics, first responders, and medical providers) may be to control and stop bleeding. There are many devices and methods that may be employed to control bleeding. One of the most commonly used devices for bleeding control may be the elastic bandage.

Elastic bandages have been known in the prior art for many years. These bandages may be sometimes called "roller" bandages or "wraps" and come in rolls having various fasteners, such as Velcro®, metal clips, or tape. They may be sold under brand names such as ACE® wrap.

Elastic bandages may be a preferred wound dressing by caregivers ranging from physicians and trained medics to individual first responders with minimal first aid training. Elastics bandages may be highly adaptable to treat a range of wounds and conform to virtually any body part. Elastic bandages provide many benefits at the wound site, including applying varying degrees of compression and support to the wound, as well as providing a sterile barrier around the wound. Compression and support may be effective in controlling bleeding, and reducing pain and swelling in the area around the wound. The sterile barrier reduces the risk of contamination and infection of the wound.

Elastic bandages may be also effective in applying and securing other treatment medicaments and materials to the wound site. One material that may be often used in wound dressing and treatment may be a woven fabric or gauze. Gauze may be effective in controlling bleeding and may be placed directly on the wound to provide focused treatment at the wound site. Gauze may be also used as a sterile material to remove foreign matter from the wound site.

Many currently available bandages act to cover the wound site. Their main function may be to keep the wound site clean, not to control hemorrhage. In order to control hemorrhage, another material, such as gauze, must be used at the wound site. The gauze may then be covered and wrapped by the bandage. These bandages require the introduction and use of other materials to properly treat at least one of a wound and an injury.

There may be presently available hemostatic dressings that may be designed to promote the accelerated clotting of blood at wounds. Examples of these dressing may be the HemCon® bandage (HemCon Inc., Tigard, Oreg., U.S.A) and QuickClot® (Z-Medica Corporation, Wallingford, Conn., U.S.A.). While these products generally promote clotting, they still require the application of direct pressure to the wound site in order to be effective.

Notwithstanding the usefulness of the above-described treatments, a need still exists for a fully integrated systems and methods for wound and/or injury treatment, systems and methods for treating wounds and/or injuries relatively quickly and effectively while reducing the risk of contamination and infection.

BRIEF DESCRIPTION OF THE DISCLOSURE

In one embodiment, the present disclosure provides a combination wound and injury treatment apparatus that may include thermal packs that may be positioned onto a patient's body part to provide circumferential thermal treatment. A combination wound and injury treatment apparatus in accordance with the disclosure comprises a tubular body having a first opening, a second opening, an inner surface and an outer surface. The first opening, the inner surface and the second opening cooperate to define a passage through the tubular body for the body part. The inner surface of the tubular body may be defined by a continuous flexible material such as, for example, a copolymer of polyester and polyurethane. The outer surface may be defined by similar material or related less flexible material. A temperature-retaining fluid such as a water-based gel may be received between the inner surface. A selectively pressurizable compartment may be formed by the inner surface and the outer surface of the tubular body. When inflated, the air pressurizable compartment circumferential compresses and supports for the body part. An insulating layer (e.g., a fabric wrap such as gauze) may be disposed between the inner surface of the combination wound and injury treatment apparatus and the patient's body part to protect the patient's skin from frostbite and/or to stop the bleeding.

The present disclosure also provides a method of treating an injured body part. The method according to the disclosure comprises providing a combination wound and injury treatment apparatus in accordance with the disclosure, positioning the passage through the tubular body of the combination wound and injury treatment apparatus around the injured body part, and positioning the combination wound and injury treatment apparatus on the injury and/or wound of the body part at a location where circumferential thermal treatment and/or compression may be desired. The diameter of the passage through the combination wound and injury treatment apparatus may be substantially the same size or larger than the diameter of the injured body part. When the diameter of the passage through the combination wound and injury treatment apparatus may be substantially the same size relative the diameter of the injured body part, the inner surface of the tubular body may make loose contact with the body part or an insulating layer disposed between the inner surface of the tubular body and the body part, causing the continuous flexible material to surround the body part. The tubular body gently conforms to the contours of the body part and provides substantially even compression to the body part, but, once pressurized, does not slide relative to the surface of the body part. The pressurizable compartment may be inflated to provide compression for the body part and also to insure that the inner surface of the combination wound and injury treatment apparatus may be positioned circumferentially into contact with the body part or an insulating layer disposed between the body part and the inner surface of the combination wound and injury treatment apparatus.

As noted, a combination wound and injury treatment apparatus according to the disclosure may be positioned at the desired location on a body part simply by positioning the combination wound and injury treatment apparatus around the body part proximate to the injury and/or wound. During positioning, the continuous flexible material may loosely engage the surface of the body part in a gentle but not compressive manner, but does not slide relative to the surface body part as the combination wound and injury treatment apparatus may be positioned around the injured and/or wounded body part. Once the pressurized compartment is inflated, the continuous flexible material may stretch and conform to the shape of the body part, providing compressive force and circumferential thermal treatment at the desired location. The combination wound and injury treatment apparatus according to the disclosure may be retained in the desired location on the injured body part without the need for additional securing means or overwrapping, and thus may be quickly and easily installed by a patient using. This allows for quick easy treatment of injured body parts.

A first aspect of the present disclosure is a combination wound and injury treatment apparatus, comprising: at least one outer wall having an outer surface and an inner surface and an upper end a lower end; at least one inner wall having an outer surface and an inner surface and an upper end and a lower end; at least one upper end member having an inner surface and an outer surface; at least one lower end member having an inner surface and an outer surface, the upper end member and the lower end member operatively connecting the outer wall and the inner wall such that the inner surface of the outer wall, the inner surface of the inner wall, the inner surface of the upper wall and the inner surface of the lower wall cooperate to form at least one chamber therebetween, the outer surface of the inner wall being configured to encase at least a portion of a patient's body wherein at least a portion of outer surface of the inner wall includes a sterile material operatively associated therewith for contacting at least one of a wound and an injury; and wherein the at least one chamber is capable of being pressurized such that the sterile material of the outer surface of the inner wall is capable of selectively applying pressure to the wound on the patient.

A second aspect of the present disclosure is a combination wound and injury treatment method, comprising: providing a combination wound and injury treatment apparatus configured to accept an open wound portion of a patient, the apparatus comprising: at least one outer wall having an outer surface and an inner surface and an upper end a lower end; at least one inner wall having an outer surface and an inner surface and an upper end and a lower end; at least one upper end member having an inner surface and an outer surface; at least one lower end member having an inner surface and an outer surface, the upper end member and the lower end member operatively connecting the outer wall and the inner wall such that the inner surface of the outer wall, the inner surface of the inner wall, the inner surface of the upper wall and the inner surface of the lower wall cooperating to form at least one chamber therebetween, the outer surface of the inner wall being configured to encase at least a portion of a patient's body wherein at least a portion of outer surface of the inner wall includes a sterile material operatively associated therewith for contacting at least one of a wound and an injury; and wherein the at least one chamber is capable of being pressurized such that the sterile material of the outer surface of the inner wall is capable of selectively applying pressure to the wound on the patient's body; placing the wound treatment apparatus over at least one of a wound and an injured area of a patient's body; and applying pressure to the wound with the combination wound and injury treatment apparatus.

A third aspect of the present disclosure is a combination wound and injury treatment apparatus comprising: a plurality of modular combination wound and injury treatment apparatus, each modular combination wound and injury treatment apparatus comprising: at least one outer wall having an outer surface and an inner surface and an upper end a lower end; at least one inner wall having an outer surface and an inner surface and an upper end and a lower end; at least one upper end member having an inner surface and an outer surface; at least one lower end member having an inner surface and an outer surface, the upper end member and the lower end member operatively connecting the outer wall and the inner wall such that the inner surface of the outer wall, the inner surface of the inner wall, the inner surface of the upper wall and the inner surface of the lower wall cooperating to form at least one chamber therebetween, the outer surface of the inner wall being configured to encase at least a portion of a patient's body wherein at least a portion of outer surface of the inner wall includes a sterile material operatively associated therewith for contacting at least one of a wound and an injury; and wherein the at least one chamber is capable of being pressurized such that the sterile material of the outer surface of the inner wall is capable of selectively applying pressure to the wound on the patient's body.

A fourth aspect of the present disclosure is a combination wound and injury treatment apparatus comprising: a tubular body having a first opening, a second opening, a relatively inflexible outer wall having an outer surface and an inner surface, a relatively flexible inner wall having an inner surface and an outer surface, an upper end member having an inner surface and an outer surface and a lower end member having an inner surface and an outer surface, the first opening, the inner surface of the relatively flexible inner wall and the second opening define a passage through the tubular body for receiving a body part; structure formed between the inner surface and the outer surface of the inner wall, the structure being capable of receiving a temperature retaining fluid; a chamber, operatively formed between the inner surface of the outer wall and the outer surface of the inner wall, the chamber being capable of being pressurized; at least one valve, operatively positioned in the outer wall, the at least one valve being capable of regulating the pressure inside the chamber; and a sterile substance, operatively positioned contiguous with the outer surface of the inner wall and being capable of being positioned proximate at least one of a wound and an injury.

The foregoing and other features of the disclosure may be hereinafter more fully described and particularly pointed out in the claims, the following description setting forth in detail certain illustrative embodiments of the disclosure, these being indicative, however, of but a few of the various ways in which the principles of the present disclosure may be employed.

BRIEF DESCRIPTION OF THE DRAWINGS

The subject matter which may be regarded as the disclosure may be particularly pointed out and distinctly claimed in the claims at the conclusion of the specification. The foregoing and other features and advantages of the disclosure may be apparent from the following detailed description taken in conjunction with the accompanying drawings in which:

DETAILED DESCRIPTION OF THE DISCLOSURE

A detailed description of the hereinafter described embodiments of the disclosed apparatus and method may be presented herein by way of exemplification and not limitation with reference to the Figures.

Figure 1A:
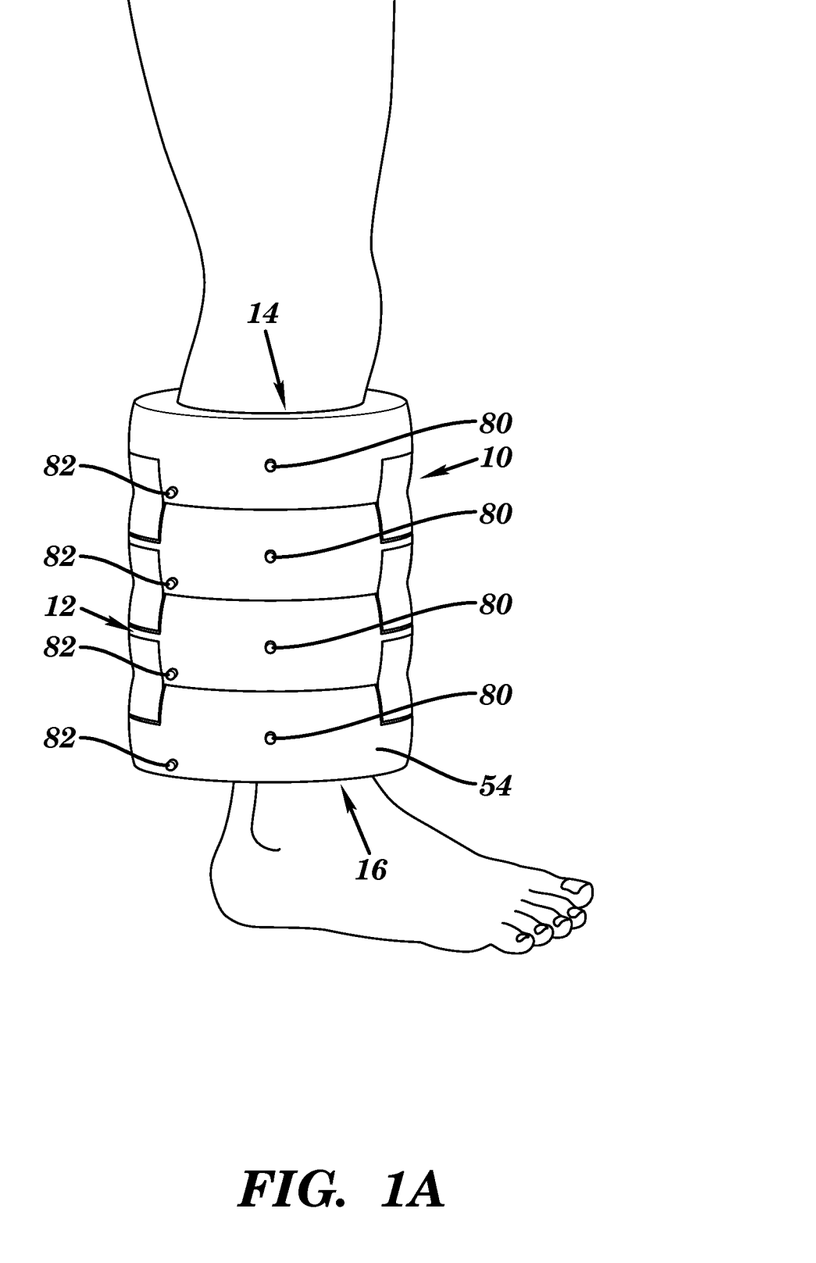
FIG. 1A is a perspective view of the combination wound and injury treatment apparatus illustrated on the ankle and calf of a patient in accordance with one embodiment of the present disclosure.
Figure 1B:
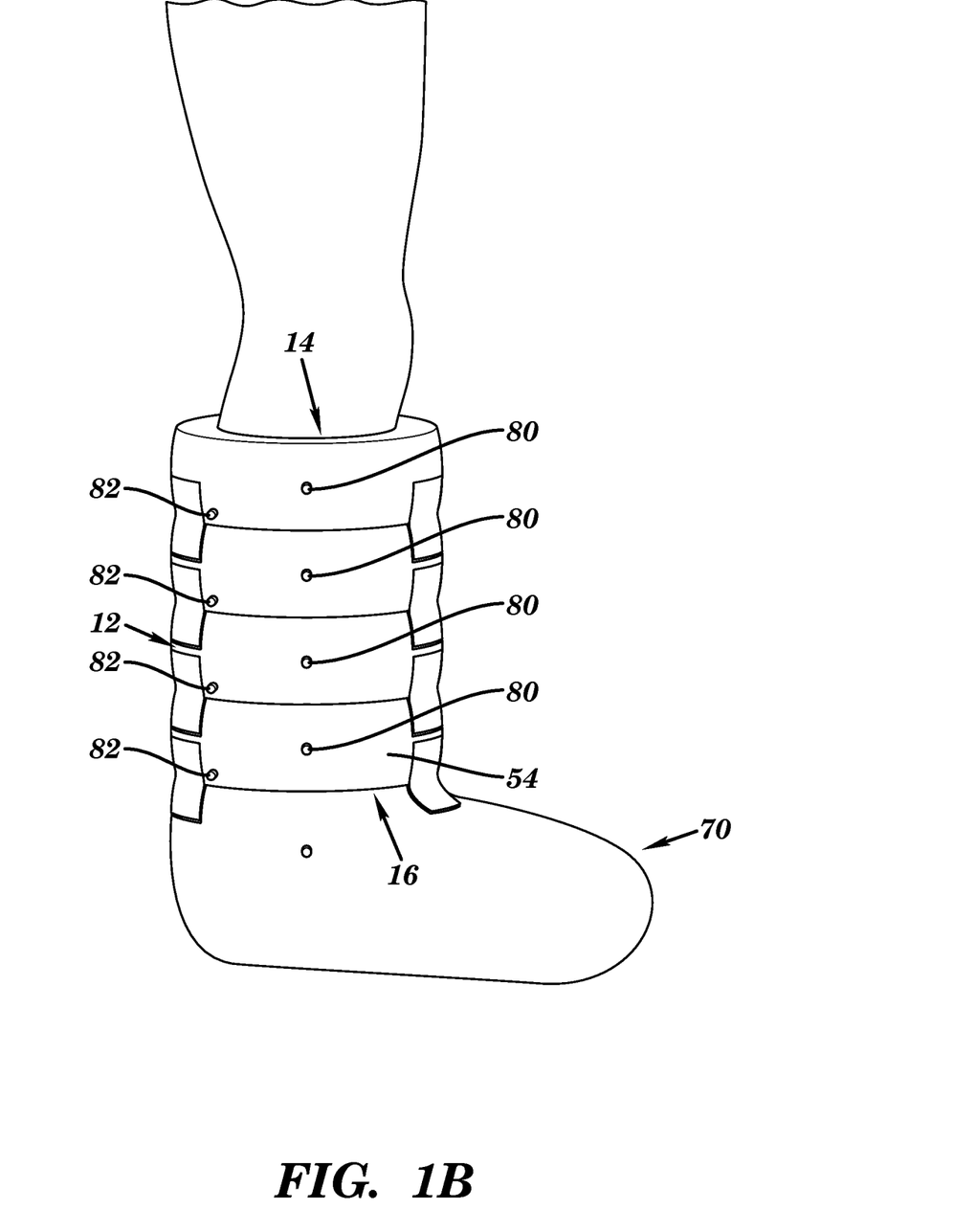
FIG. 1B is a perspective view of the combination wound and injury treatment apparatus illustrated on the foot, ankle and calf of a patient in accordance with an embodiment of the present disclosure.
Figure 2:
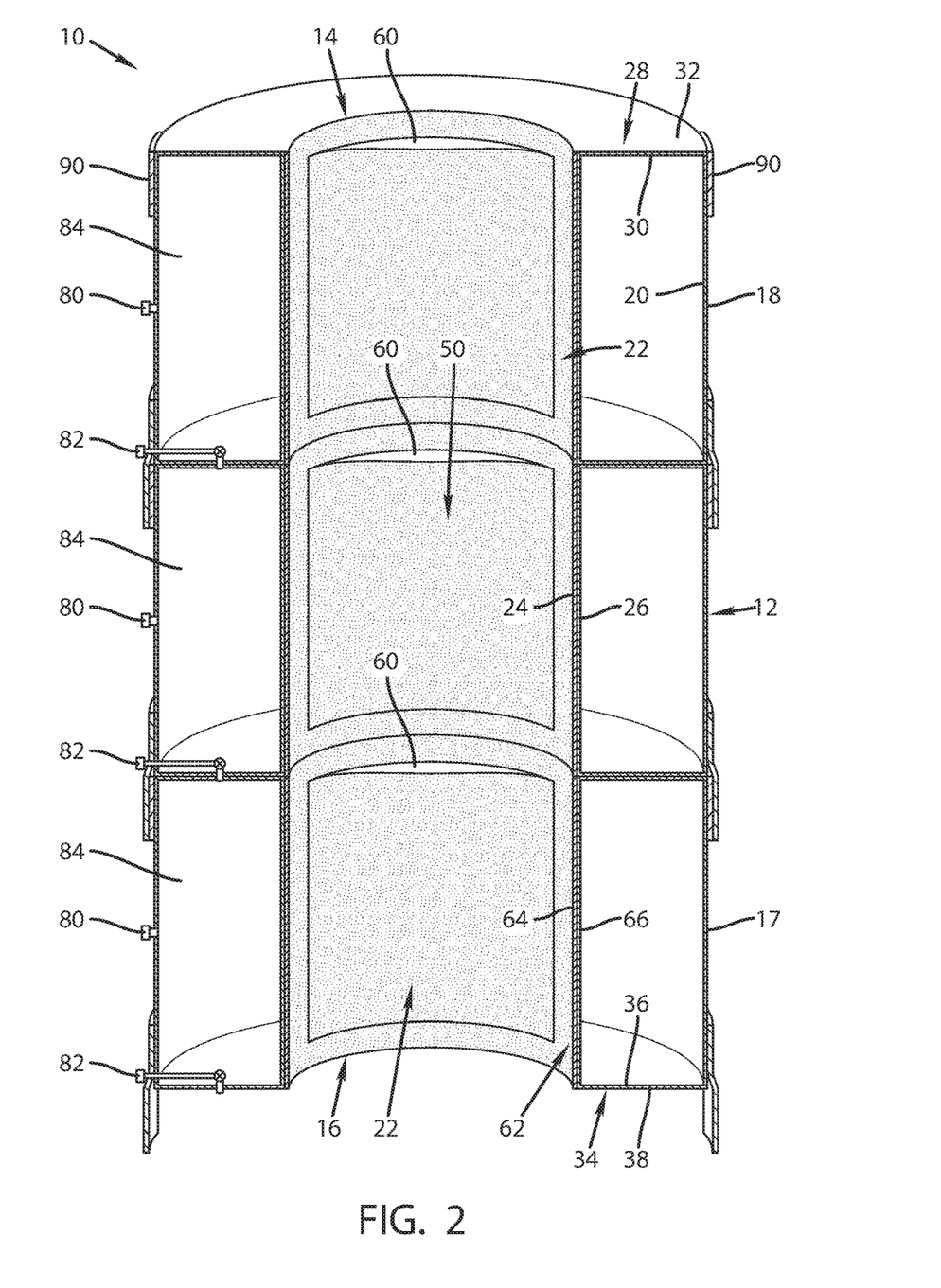
FIG. 2 depicts a perspective view of a cross-section of the wound and injury treatment apparatus illustrated in FIG. 1A in accordance with an embodiment of the present disclosure.

With reference to FIGS. 1A, 1B and 2, several embodiments of the combination wound and injury treatment apparatus of the present disclosure is illustrated. One embodiment of the combination wound and injury treatment apparatus 10 according to the disclosure may comprise a tubular body 12 having a first opening 14, a second opening 16, an outer wall 17 having in outer surface 18 and an inner surface 20 and an inner wall 22 having an inner surface 24 and in outer surface 26, an upper end member 28 having an inner surface 30 and an outer surface 32 and a lower end member 34 having an inner surface 36 and an outer surface 38, although the disclosure is not limited in this regard. The first opening 14, the inner wall 22 and the second opening 16 may cooperate to define a passage 50 through the tubular body 12 for a body part, although the disclosure is not limited in this regard.

FIG. 2 illustrates the combination wound and injury treatment apparatus 10 as seen along the line I-I in FIG. 1A. Thus, a combination wound and injury treatment apparatus in accordance with the disclosure may comprise a tubular body 12 having an elongated generally torus-like shape that may be formed of a continuous inner relatively flexible material and a continuous outer relatively inflexible material, although the disclosure is not limited in this regard.

The continuous relatively flexible material may be a polymeric film that remains flexible over a relatively broad temperature range of from about 0° F. to about 130° F., although the disclosure is not limited in this regard. A large number of polymeric films that remain flexible over such a temperature range are known to those skilled in the art. It will be appreciated that polymeric materials used in the disclosure may be single layer films or multi-layer structures, although the disclosure is not limited in this regard. Regardless of the number of layers, the polymeric materials must be capable of preventing air from moving from one side 26 of the polymeric materials through the polymeric materials and escaping out the other side 24 of the polymeric materials, although the disclosure is not limited in this regard.

In one embodiment, the continuous relatively flexible material may exhibit a Shore A durometer hardness of about 85 as measured in accordance with the ASTM 2240.00 standard, although the disclosure is not limited in this regard. In another embodiment, the continuous flexible material may exhibit a Shore A durometer hardness of about 93 as measured in accordance with the ASTM 2240.00 standard, although the disclosure is not limited in this regard. Polymeric materials possessing such properties may be advantageously puncture resistant and capable of preventing the flow of air there through, yet remain flexible, although the disclosure is not limited in this regard.

In one embodiment, the continuous flexible material preferably may have a thickness of from about 3 to about 15 mils, although the disclosure is not limited in this regard. In another embodiment, the continuous flexible material may have a thickness of about 5.0 mils, although the disclosure is not limited in this regard. It will be appreciated that flexible material thickness is not per se critical, and that a variety of flexible material thicknesses may be used to fabricate the inner wall 22 a combination wound and injury treatment apparatus in accordance with the disclosure as long as the combination wound and injury treatment apparatus may be conformable to the particular body part and may be capable of applying compression against injuries and/or wounds, although the disclosure is not limited in this regard.

In another embodiment of the disclosure, the continuous relatively flexible material may comprise a 5 mil thick copolymer of polyester and polyurethane having a Shore A durometer hardness of about 95 as measured in accordance with the ASTM 2240.00 standard, although the disclosure is not limited in this regard. This relatively flexible material provides several advantages. It may be heat-sealed to itself, which facilitates fabrication of the combination wound and injury treatment apparatus, although the disclosure is not limited in this regard. It does not irritate human skin on contact. And, it remains smooth and flexible over the temperature range of from about 0° F. to about 130° F., although the disclosure is not limited in this regard.

A temperature-retaining fluid may be received into the space 60 between the inner surface 24 and the outer surface 26 of the inner wall 22, although the disclosure is not limited in this regard. Throughout the instant specification and in the appended claims, the term "temperature-retaining fluid" means any non-gaseous material that changes shape or direction uniformly in response to an external force imposed upon it and that may have the capacity to retain heat or cold for transfer to a body part, although the disclosure is not limited in this regard. The term applies not only to liquids, but also to finely divided solids, gels and combinations of liquids and solid particles having such properties, although the disclosure is not limited in this regard. In one embodiment, the temperature-retaining fluid may be a gel, and in another embodiment, a water-based gel, although the disclosure is not limited in this regard.

Water-based gels may be formulated so as to provide a temperature-retaining fluid that may be more viscous than water and does not become a hard solid within the temperature range of from 0° F. and 32° F., although the disclosure is not limited in this regard. Such gels may conform to the contours of the injured body part more comfortably than ice, although the disclosure is not limited in this regard. In addition, such gels tend to retain their desired thermal properties for a longer period of time than water, although the disclosure is not limited in this regard. The gel-filled combination wound and injury treatment apparatus may be pre-heated or pre-chilled, depending upon the type of thermal treatment to be provided, although the disclosure is not limited in this regard. The composition of the gel may be not per se critical, but preferably a non-toxic formulation may be used to minimize potential injury in the event of exposure, although the disclosure is not limited in this regard.

In another embodiment of the disclosure, water-filled capsules may be dispersed in the temperature-retaining fluid, although the disclosure is not limited in this regard. When the combination wound and injury treatment apparatus is pre-chilled (e.g., through storage in a conventional freezer), the water in the water-filled capsules freezes and becomes solid ice, although the gel remains a viscous fluid, although the disclosure is not limited in this regard. The frozen water-filled capsules extend the period of time during which the combination wound and injury treatment apparatus remains cold, although the disclosure is not limited in this regard. The water-filled capsules may be preferably small, such as the size of peas, and substantially spherical, which allows the combination wound and injury treatment apparatus to comfortably conform to body parts, although the disclosure is not limited in this regard.

Other free-flowing solid structures may be dispersed in the temperature-retaining fluid. Examples include inorganic particulates (e.g., sand and/or ceramic particles), spherical structures (e.g., glass and/or metal spheres), magnets and combinations thereof, although the disclosure is not limited in this regard. It will be appreciated that virtually any relatively small substantially free-flowing solid structure may be dispersed in the temperature-retaining fluid, but water-filled capsules may be most preferred in view of cost, safety, and effectiveness, although the disclosure is not limited in this regard.

It may be often desirable to dispose an insulating layer between the body part and the combination wound and injury treatment apparatus, particularly when the temperature retaining combination wound fluid positioned in the injury treatment apparatus 60 may have been pre-chilled below the freezing point of water, although the disclosure is not limited in this regard. The insulation layer 62 having an inner surface 64 and an outer surface 66, which may be formed of fabric, such as, for example, a sterile material possibly in combination with a polymeric foam, may prevent frostbite among other conditions, although the disclosure is not limited in this regard. In one embodiment, the insulation layer 62 may be disposed as a removable layer inside the tubular body of the combination wound and injury treatment apparatus 10 so as to be coextensive with the inner surface 22 of the tubular body, although the disclosure is not limited in this regard. In another embodiment, additional insulation layer 62 may be wrapped around the body part prior to applying the combination wound and injury treatment apparatus (e.g. a sleeve, a sock or an ACE bandage), although the disclosure is not limited in this regard.

FIG. 2 illustrates a cross-sectional view of a combination wound and injury treatment apparatus 10 according to the disclosure as it may be about to be placed onto a body part, although the disclosure is not limited in this regard. When the diameter of the passage through the tubular body 12 may be larger than the diameter of the body part to insure a comfortable fitting, the continuous relatively flexible material having the insulation layer 62 as the inner most surface 64 for containing the injury and/or wound and which may frictionlessly surround the outer surface of the body part and/or an insulating layer disposed between the body part and the continuous relatively flexible material, although the disclosure is not limited in this regard. Thus, the continuous relatively flexible material may substantially move relative to the surface of the body part, but the tubular body defined by the continuous relatively flexible material does not engage the body part such that friction may be developed between the relatively flexible material and the body part as the combination wound and injury treatment apparatus 10 is placed contiguous with the body part, although the disclosure is not limited in this regard.

FIG. 1B illustrates a perspective view of a combination wound and injury treatment apparatus 10 positioned on a body part, which, in this illustration may be a leg, although the disclosure is not limited in this regard. In this instance, the patient first inserted his foot into the passage (not shown) through the tubular body 70 surrounding the foot of the patient of the combination wound and injury treatment apparatus 10, although the disclosure is not limited in this regard. The insulation layer 62 contiguous to the continuous relatively flexible material may loosely engage the patient's foot, ankle and calf, causing the tubular bodies 12 and 70 to encompass the patient's foot, ankle and calf such that the desired location when the injuries and/or wounds are located on the body part, which in this illustration may be located on the patient's foot, ankle and calf, although the disclosure is not limited in this regard. Once positioned, as illustrated in FIG. 1B, the combination wound and injury treatment apparatus 10 thus provides circumferential thermal treatment and/or comfortable pressurized compression to the patient's foot, ankle and/or calf, the specifics of the pressurization will be described in more detail below, although the disclosure is not limited in this regard.

It will be appreciated that the combination wound and injury treatment apparatus 10 according to the disclosure may be formed with passages having various configurations depending upon the intended use, although the disclosure is not limited in this regard. In order to insure that the proper compressive force may be applied to the body part, the combination wound and injury treatment apparatus should be properly sized, although the disclosure is not limited in this regard. Larger sized combination wound and injury treatment apparatus may be used on legs, and smaller sized combination wound and injury treatment apparatus may be used on arms and children, although the disclosure is not limited in this regard. Combination wound and injury treatment apparatus according to the disclosure may be custom-sized to provide injury and/or wound treatment to human hands, fingers, wrists, elbows, forearms, upper arms, feet, ankles, calves, knees, and thighs, as well as other body parts, although the disclosure is not limited in this regard. A combination wound and injury treatment apparatus having a longitudinal length of about 4.0 inches and an inner diameter of about 1.0 inch may be particularly suitable for use in providing thermal treatment to a human finger, although the disclosure is not limited in this regard. In addition, combination wound and injury treatment apparatus according to the disclosure may be customized to provide combination wound and/or injury treatment to the body parts and/or bodies of non-human animals, as would be understood by those skilled in the art, although the disclosure is not limited in this regard.

When configured for use on a human wrist, the passage through the tubular body may be preferably substantially cylindrical in shape with an inner diameter within the range of from about 2.5 to about 4.0 inches, although the disclosure is not limited in this regard. The passage through the tubular body preferably may have a length of from about 4.0 to about 6.0 inches, although the disclosure is not limited in this regard. Approximately 16 ounces of water-based gel material may be disposed into the space between the inner surface and the outer surface, which results in a gel layer that may be about 0.5 inches thick around the entire wrist when the combination wound and injury treatment apparatus may be positioned on the patient's wrist, although the disclosure is not limited in this regard.

Combination wound and injury treatment apparatus configured for use on an elbow generally have a passage through the tubular body that may be larger in diameter and greater in length than a combination wound and injury treatment apparatus configured for use on a wrist, although the disclosure is not limited in this regard. Combination wound and injury treatment apparatus configured for use on forearms preferably have a tapered passage, which may result of the combination of a plurality of individual combination wound and injury treatment apparatus, although the disclosure is not limited in this regard. Combination wound and injury treatment apparatus configured for elbows (not shown), ankles, knees (not shown), calves, thighs (not shown), and other body parts may be preferably shaped and sized so as to be comfortable when positioned thereon, although the disclosure is not limited in this regard. It will be appreciated that the size of the passage and the amount of gel disposed into the space between the inner surface and the outer surface may be adjusted to suit a particular end use application, although the disclosure is not limited in this regard.

A plurality of combination wound and injury treatment apparatus each interconnected to the other is illustrated in FIGS. 1A, 1B and 2, although the disclosure is not limited in this regard. While it may not be necessary to utilize more than one combination wound and injury treatment apparatus to treat each injury and/or wound, it may be more effective to utilize at least two pre-fabricated individual wound and injury treatment apparatus operatively connected to address a specific injury and/or wound without having to fabricate a custom combination wound and injury treatment apparatus on each occasion of treatment, although the disclosure is not limited in this regard. Thus, in FIG. 1A, four individually fabricated wound and injury treatment apparatus are operatively connected to treat a specific injury and/or wound on the ankle/calf area of a patient's leg, although the disclosure is not limited in this regard.

FIG. 1B illustrates the four individually fabricated wound and injury treatment apparatus in FIG. 1A operatively connected in combination with an additional wound and injury treatment apparatus 70 for treatment of a patient's foot, although the disclosure is not limited in this regard. While the foot wound and injury treatment apparatus 70 is shown operatively connected to additional wound and injury treatment apparatus as enclosing the entire foot, the foot portion may be the only portion that may be needed if the wound or injury is only to the foot, although the disclosure is not limited in this regard. Additionally, the toe of the foot wound and injury treatment apparatus need not be enclosed, depending upon the extent of the wound and/or injuries to the foot, although the disclosure is not limited in this regard.

As stated above, FIG. 2 illustrates a cross-section of three individual wound and injury treatment apparatus operatively connected together, although the disclosure is not limited in this regard. A connecting structure 90, for operatively connecting at least a second wound and injury treatment apparatus to a first wound and injury treatment apparatus, is operatively attached to at least a portion thereof. As illustrated, in order to operatively connect two or more individual wound and injury treatment apparatus together such that when pressurized, the pressure may be constant throughout the entire length of the multi-stage apparatus, two pressure regulating devices, such as for example, valves 80, 82 are operatively positioned such that each chamber 84 of the each wound and injury treatment apparatus can be regulated, although the disclosure is not limited in this regard. The first valve 80 may be utilized to control the amount of pressure generated by each chamber 84, especially when the individual wound and injury treatment apparatus may be applied as a single unit, although the disclosure is not limited in this regard. The second valve 82 may be utilized to interconnect and adjust the pressure of the adjacent chamber 84 of each individual wound and injury treatment apparatus when two or more individual wound and treatment apparatus are combined together, as illustrated in FIGS. 1A, 1B, and 2, although the disclosure is not limited in this regard.

As illustrated in FIG. 2, the second regulating valve 82, whose default condition may be closed, equalizes the pressure between adjacent chambers 84 such that when the pressure in one chamber may be greater or less than the pressure in the adjacent chamber 84, the regulating valve 82 opens to allow the pressure in the adjacent chambers 84 to equalize and then closes, although the disclosure is not limited in this regard.

In view of the foregoing, a combination wound and injury treatment apparatus according to the disclosure provides many advantages. The circular shaped tubular body allows the combination wound and injury treatment apparatus to be gently positioned proximate the patient's body part quickly and easily, although the disclosure is not limited in this regard. The combination wound and injury treatment apparatus does not normally require the use of auxiliary attachment means such as straps or wraps, although the disclosure is not limited in this regard. The combination wound and injury treatment apparatus provides radial compression to the body part, which reduces swelling and speeds up the recovery time. And, the combination wound and injury treatment apparatus provides circumferential thermal treatment to an injured body part, although the disclosure is not limited in this regard.

Elements of the embodiments have been introduced with either the articles "a" or "an." The articles may be intended to mean that there may be one or more of the elements. The terms "including" and "having" and their derivatives may be intended to be inclusive such that there may be additional elements other than the elements listed. The conjunction "or" when used with a list of at least two terms may be intended to mean any term or combination of terms. The terms "first" and "second" may be used to distinguish elements and may be not used to denote a particular order.

While the disclosure may have been described in detail in connection with only a limited number of embodiments, it should be readily understood that the disclosure may be not limited to such disclosed embodiments. Rather, the disclosure may be modified to incorporate any number of variations, alterations, substitutions or equivalent arrangements not heretofore described, but which may be commensurate with the spirit and scope of the disclosure. Additionally, while various embodiments of the disclosure have been described, it may be to be understood that aspects of the disclosure may include only some of the described embodiments. Accordingly, the disclosure may be not to be seen as limited by the foregoing description, but may be only limited by the scope of the appended claims.

What may be claimed is:

1. A combination wound and injury treatment apparatus, comprising:
    a first tubular body member having a first end and a second end, the first tubular body having a first central passage extending between the first end and the second end, wherein the first central passage has a diameter that allows a limb of a person to be received within the first central passage, the first tubular body defined by:
        an outer wall having an outer surface and an inner surface,
        an inner wall having an outer surface and an inner surface,
        an upper end member having an inner surface and an outer surface, the upper end member located proximate the first end,
        a lower end member having an inner surface and an outer surface, the lower end member located proximate the second end;
    a first chamber surrounding the central passageway, the first chamber defined by the inner surface of the outer wall, the outer surface of the inner wall, the inner surface of the upper end member, and the inner surface of the lower end member; a first pressure regulator connected to only the first chamber wherein the first pressure regulator is operatively accessible external to the first chamber;
    a second tubular body having a second chamber and second central passageway attached to the first tubular body by a connecting structure such that the first central passageway is aligned with the second central passageway;
    a second pressure regulator connected to only the second chamber, wherein the second pressure regulator is operatively accessible external to the second chamber, wherein the first pressure regulator and the second pressure regulator adjust the pressure within the first chamber and the second chamber, respectively, so that the pressure is equalized between the first chamber and the second chamber, wherein the first pressure regulator and second pressure regulator each independently or simultaneously regulate the pressures of both the first chamber and the second chamber;
    a third pressure regulator interconnecting the first chamber and the second chamber, wherein the third pressure regulator is operatively accessible external to the first chamber and second chamber, wherein the third pressure regulator is configured to adjust the pressure of each of the first chamber and second chamber;
    wherein the third pressure regulator is configured to equalize the pressure between the first chamber and the second chamber;
    wherein a sterile material is removably disposed on the inner surface of the inner wall for contacting a wound of a user, the sterile material being an insulation layer, wherein the insulation layer is configured to receive a limb of a person independently of the first central passage;
    wherein a temperature retaining fluid is disposed directly within a space between the inner surface of the inner wall and the outer surface of the inner wall, such that the temperature retaining fluid fills the space between the inner surface of the inner wall and the outer surface of the inner wall, the temperature retaining fluid being a water-based gel;
    wherein the first chamber and the second chamber pressurized to provide a radial compressive force against the wound, the radial compressive force resulting in the sterile material selectively applying pressure to the wound while the wound received circumferential thermal treatment from the temperature retaining fluid disposed within the space.

2. The combination wound and injury treatment apparatus of claim 1, wherein the temperature retaining fluid includes a cold liquid, or a cold gas.

3. The combination wound and injury treatment apparatus of claim 2, wherein the space includes: at least one pocket, the at least one pocket being configured to house the temperature retaining fluid.

4. The combination wound and injury treatment apparatus of claim 1, wherein each of the first pressure regulator and the second pressure regulator have an open-close switch.

5. The combination wound and injury treatment apparatus of claim 1, wherein the temperature retaining fluid flows freely within the space wherein water-filled capsules are disposed in the temperature-retaining fluid.

6. The combination wound and injury treatment apparatus of claim 1, wherein the first central passageway and the second central passageway are adjustable in diameter.

7. The combination wound and injury treatment apparatus of claim 1, wherein the insulation layer is configured to stop bleeding.

8. The combination wound and injury treatment device of claim 1, wherein the inner wall of the outer surface comprises an impermeable continuous flexible material configured to resist puncturing.

9. A combination wound and injury treatment method, comprising:
    providing a wound and injury treatment apparatus including a first tubular body member having a first end and a second end, the tubular body having a first central passage extending between the first end and the second end, wherein the first central passage has a diameter that allows a limb of a person to be received within the first central passage, the first tubular body defined by:
- an outer wall having an outer surface and an inner surface,
- an inner wall having an outer surface and an inner surface,
- an upper end member having an inner surface and an outer surface, the upper end member located proximate the first end,
- a lower end member having an inner surface and an outer surface, the lower end member located proximate the second end;
- a first chamber surrounding the central passageway, the first chamber defined by the inner surface of outer wall, the outer surface of the inner wall, the inner surface of the upper end member, and the inner surface of the lower end member;
- a first pressure regulator connected to only the first chamber wherein the first pressure regulator is operatively accessible external to the first chamber;
- a second tubular body having a second chamber and second central passageway attached to the first tubular body by a connecting structure such that the first central passageway is aligned with the second central passageway;
- a second pressure regulator connected to only the second chamber, wherein the second pressure regulator is operatively accessible external to the second chamber, wherein the first pressure regulator and the second pressure regulator adjust the pressure within the first chamber and the second chamber, respectively, so that the pressure is equalized between the first chamber and the second chamber, such that the pressure between the first chamber and second chamber remains equalized once equalized, wherein the first pressure regulator and second pressure regulator each can independently or simultaneously regulate the pressures of both the first chamber and the second chamber;
- a third pressure regulator interconnecting the first chamber and the second chamber, wherein the third pressure regulator is operatively accessible external to the first chamber and second chamber, wherein the third pressure regulator is configured to adjust the pressure of each of the first chamber and second chamber;
   - wherein the third pressure regulator is configured to equalize the pressure between the first chamber and the second chamber;
- releasably disposing a sterile material on the inner surface of the inner wall for contacting a wound of a user, the sterile material being an insulation layer, wherein the insulation layer is configured to receive a limb of a person independently of the first central passage;
- disposing a temperature retaining fluid directly within a space between the inner surface of the inner wall and the outer surface of the inner wall, such that the temperature retaining fluid fills the space between the inner surface of the inner wall and the outer surface of the inner wall, the temperature retaining fluid being a water-based gel;
- pressurizing the first chamber and the second chamber to provide a radial compressive force against the wound, the radial compressive force resulting in the sterile material selectively applying pressure to the wound while the wound received circumferential thermal treatment from the temperature retaining fluid disposed within the space.

10. The combination wound and injury treatment method of claim 9, wherein the temperature retaining fluid flows freely within the space wherein water-filled capsules are disposed in the temperature-retaining fluid.

11. The combination wound and injury treatment method of claim 9, wherein the first central passageway and the second central passageway are adjustable in diameter.

12. The combination wound and injury treatment method of claim 9, wherein the insulation layer is configured to stop bleeding.

13. The combination wound injury treatment method of claim 9, wherein the wherein the inner wall of the outer surface comprises an impermeable continuous flexible material configured to resist puncturing.

* * * * *